US011921202B2

(12) United States Patent
Yamamoto et al.

(10) Patent No.: US 11,921,202 B2
(45) Date of Patent: Mar. 5, 2024

(54) PHOTOACOUSTIC IMAGE GENERATION APPARATUS

(71) Applicant: FUJIFILM Corporation, Tokyo (JP)

(72) Inventors: Katsuya Yamamoto, Ashigarakami-gun (JP); Kaku Irisawa, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 1044 days.

(21) Appl. No.: 16/542,855

(22) Filed: Aug. 16, 2019

(65) Prior Publication Data

US 2019/0369239 A1 Dec. 5, 2019

Related U.S. Application Data

(63) Continuation of application No. PCT/JP2018/007066, filed on Feb. 27, 2018.

(30) Foreign Application Priority Data

Mar. 29, 2017 (JP) ................... 2017-064579

(51) Int. Cl.
G01S 15/89 (2006.01)

(52) U.S. Cl.
CPC ...... G01S 15/8913 (2013.01); G01S 15/8918 (2013.01); G01S 15/892 (2013.01); G01S 15/8952 (2013.01)

(58) Field of Classification Search
CPC ............ G01S 15/8913; G01S 15/8952; G01S 15/892; G01S 15/8918; A61B 5/0095; A61B 5/742; G01N 29/24; G01N 21/17
See application file for complete search history.

(56) References Cited

U.S. PATENT DOCUMENTS 6,520,915 B1 2/2003 Lin et al.
9,055,869 B2 * 6/2015 Li .................. A61B 5/14551
(Continued)

FOREIGN PATENT DOCUMENTS

JP 9-133654 A 5/1997
JP 2015-37519 A 2/2015
(Continued)

OTHER PUBLICATIONS

International Preliminary Report on Patentability and English translation of the Written Opinion of the International Searching Authority (Forms PCT/IB/326, PCT/IB/373, and PCT/ISA/237) for International Application No. PCT/JP2018/007066, dated Oct. 10, 2019.
(Continued)

Primary Examiner — Baisakhi Roy
(74) Attorney, Agent, or Firm — Birch, Stewart, Kolasch & Birch, LLP

(57) ABSTRACT

An insert having a photoacoustic wave generation portion, an acoustic wave detection unit that detects photoacoustic waves and reflected acoustic waves, an acoustic image generation unit that generates a B mode acoustic image on the basis of the reflected acoustic waves, a photoacoustic image generation unit that generates a photoacoustic image on the basis of the photoacoustic waves, an image output unit that outputs a display image obtained by synthesizing the B mode acoustic image and the photoacoustic image, and a control unit that controls a detection frequency of the photoacoustic waves used in a case where the photoacoustic image is generated in the photoacoustic image generation unit on the basis of a resolution of the B mode acoustic image forming the display image are included.

20 Claims, 6 Drawing Sheets

(56) References Cited

U.S. PATENT DOCUMENTS

| | | | |
|---|---|---|---|
| 9,867,545 B2* | 1/2018 | Sato | A61B 5/0095 |
| 10,806,346 B2* | 10/2020 | Boctor | A61B 8/5207 |
| 2003/0050557 A1* | 3/2003 | Susil | A61B 5/055 |
| | | | 600/424 |
| 2007/0088416 A1* | 4/2007 | Atalar | A61B 5/283 |
| | | | 607/115 |
| 2008/0114235 A1* | 5/2008 | Unal | G01R 33/286 |
| | | | 600/411 |
| 2011/0319743 A1* | 12/2011 | Satoh | A61B 5/0035 |
| | | | 600/407 |
| 2013/0039147 A1* | 2/2013 | Witte | G01N 29/2418 |
| | | | 367/7 |
| 2014/0180135 A1* | 6/2014 | Hoseit | A61B 5/0084 |
| | | | 600/478 |
| 2015/0297092 A1 | 10/2015 | Irisawa | |
| 2015/0374312 A1* | 12/2015 | Sato | G01N 21/1702 |
| | | | 600/407 |
| 2016/0058290 A1* | 3/2016 | Nakatsuka | H05B 45/46 |
| | | | 600/407 |
| 2016/0061715 A1* | 3/2016 | Kitagawa | G01N 29/0654 |
| | | | 73/606 |
| 2017/0303794 A1* | 10/2017 | Suehira | A61B 8/14 |
| 2018/0270474 A1* | 9/2018 | Liu | A61B 6/508 |
| 2019/0369239 A1* | 12/2019 | Yamamoto | G01S 15/8952 |

FOREIGN PATENT DOCUMENTS

| | | |
|---|---|---|
| JP | 2015-231583 A | 12/2015 |
| JP | 2016-67552 A | 5/2016 |

OTHER PUBLICATIONS

International Search Report (Form PCT/ISA/210) for International Application No. PCT/JP2018/007066, dated Apr. 24, 2018, with English translation.

Author Unknown, "Ultrasonic equipment handbook", Handbook of Ultrasonic Diagnostic Equipments, Jan. 20, 1997, pp. 148-151 (5 pages).

Japanese Office Action, dated Jul. 21, 2020, for corresponding Japanese Application No. 2019-509012, with an English translation.

* cited by examiner

FIG. 8

| $R_b$ (pixel/mm) | $f_n$ (MHz) |
|---|---|
| 15 | 7.8 |
| 13 | 7.5 |
| 11 | 7 |
| 9 | 6.5 |
| 7 | 6 |
| 5 | 5 |

PHOTOACOUSTIC IMAGE GENERATION APPARATUS

CROSS-REFERENCE TO RELATED APPLICATIONS

This application is a Continuation of PCT International Application No. PCT/JP2018/007066 filed on Feb. 27, 2018, which claims priority under 35 U.S.C § 119(a) to Japanese Patent Application No. 2017-064579 filed on Mar. 29, 2017. Each of the above application(s) is hereby expressly incorporated by reference, in its entirety, into the present application.

BACKGROUND OF THE INVENTION

1. Field of the Invention

The present invention relates to a photoacoustic image generation apparatus comprising an insert of which at least a portion is inserted into a subject and which includes a photoacoustic wave generation portion that absorbs light and generates photoacoustic waves.

2. Description of the Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

In addition, as a technique related to the photoacoustic imaging, JP2015-231583A discloses a puncture needle in which a photoacoustic wave generation portion that absorbs light and generates photoacoustic waves is provided in the vicinity of a tip. In the puncture needle, an optical fiber is provided up to the tip of the puncture needle and light guided by the optical fiber is emitted to the photoacoustic wave generation portion. An ultrasound probe detects the photoacoustic waves generated by the photoacoustic wave generation portion and a photoacoustic image is generated on the basis of a detection signal of the photoacoustic waves. In the photoacoustic image, a part of the photoacoustic wave generation portion appears as a bright point, which makes it possible to check the position of the puncture needle using the photoacoustic image.

SUMMARY OF THE INVENTION

In the photoacoustic imaging using the puncture needle as described in JP2015-231583A, it is suggested that the photoacoustic image indicating the position of the puncture needle is synthesized on a B mode ultrasound image that displays the internal state of the living body of the subject using a two-dimensional image such that the tip position of the puncture needle in the inside of the living body can be easily checked.

Here, it is possible to obtain the B mode ultrasound image with a high resolution by capturing the image using an ultrasound signal with a high frequency, but the ultrasound with the high frequency is difficult to reach a deep part of the living body. Therefore, in JP2016-067552A, it is suggested that the image capturing is performed using the ultrasound signal with the high frequency in a shallow part of the living body where attenuation of the ultrasound is low and the image capturing is performed using the ultrasound signal with a low frequency in the deep part of the living body where the attenuation of the ultrasound is high to acquire an image having as much information as possible.

In this case, for the photoacoustic image for specifying the tip position of the puncture needle, in a case where the image capturing is performed using a photoacoustic wave signal with the same frequency as the generation of B mode ultrasound image, the resolution of photoacoustic image is also changed according to the depth of the living body tissue. In the photoacoustic image indicating the tip position of the puncture needle, the tip position of the puncture needle is commonly displayed by the bright point. However, since a display size of the bright point depends on a detection frequency (wavelength) of the photoacoustic wave signal at the time of the generation of the photoacoustic image and thus an image size for one wavelength, which is the minimum resolution, becomes larger as the detection frequency is lower (wavelength is longer), the tip position thereof is displayed by a large bright point. Therefore, the display size of the bright point indicating the tip position of the puncture needle according to the depth of the living body tissue is changed, which may cause a user to feel discomfort.

In order to solve such a problem, it may be considered that the image capturing is performed using the photoacoustic wave signal with a constant frequency for the photoacoustic image for specifying the tip position of the puncture needle. However, in this case, the image capturing is often performed using the photoacoustic wave signal with the low frequency such that the tip position of the puncture needle can be detected at any depth inside the living body.

In this case, in a case where, for example, only a high resolution region of the shallow part of the living body in the B mode ultrasound image is displayed with the high resolution (pixel/mm) and the photoacoustic image with the low resolution is synthesized on the B mode ultrasound image, there may be a problem that the display size of the bright point becomes large, thus a region of the B mode ultrasound image hidden by the bright point becomes wide, and thus it is difficult to view the living body tissue around the tip of the puncture needle. In the puncture, since it is important whether the needle tip reaches the living body tissue of interest such as a blood vessel or a tumor, it is desired that the living body tissue around the tip of the puncture needle can be clearly checked as much as possible.

Conversely, in a case where a wide region up to the deep part of the living body in the B mode ultrasound image is displayed with the low resolution (pixel/mm), there may be a problem that the display size of the bright point becomes too small and thus it is difficult to check the tip position of the puncture needle.

In this way, the optimum display size of the bright point in the photoacoustic image is different according to the resolution in the case of displaying the B mode ultrasound image. Therefore, it is desired that it is possible to acquire the photoacoustic image with an appropriate resolution according to the resolution of the B mode ultrasound image.

The invention has been made in view of the above-mentioned problems and an object of the invention is to provide a photoacoustic image generation apparatus capable of acquiring a photoacoustic image with an appropriate resolution according to a resolution of a B mode ultrasound image in the photoacoustic image generation apparatus that acquires and synthesizes both the B mode ultrasound image and a photoacoustic image.

A photoacoustic image generation apparatus according to the invention comprises: an insert of which at least a tip portion is inserted into a subject and which includes a light guide member that guides light to the tip portion and a photoacoustic wave generation portion that absorbs the light guided by the light guide member and generates photoacoustic waves; an acoustic wave detection unit that detects the photoacoustic waves emitted from the photoacoustic wave generation portion and detects reflected acoustic waves reflected by transmission of acoustic waves to the subject; an acoustic image generation unit that generates a B mode acoustic image on the basis of the reflected acoustic waves detected by the acoustic wave detection unit; a photoacoustic image generation unit that generates a photoacoustic image on the basis of the photoacoustic waves detected by the acoustic wave detection unit; an image output unit that outputs a display image obtained by synthesizing the B mode acoustic image and the photoacoustic image; and a control unit that controls a detection frequency of the photoacoustic waves used in a case where the photoacoustic image is generated in the photoacoustic image generation unit on the basis of a resolution of the B mode acoustic image forming the display image.

Here, the "resolution of the B mode acoustic image forming the display image" means the number of assigned pixels per a predetermined length in the display image and is represented by, for example, a unit of pixel/mm.

In the photoacoustic image generation apparatus according to the invention, the control unit may control the detection frequency of the photoacoustic waves used in the case where the photoacoustic image is generated in the photoacoustic image generation unit to be higher as the resolution of the B mode acoustic image forming the display image becomes higher.

In the photoacoustic image generation apparatus according to the invention, the control unit may decide the detection frequency of the photoacoustic waves used in the case where the photoacoustic image is generated in the photoacoustic image generation unit such that a product of the resolution of the B mode acoustic image forming the display image and a wavelength at the detection frequency of the photoacoustic waves used in the case where the photoacoustic image is generated becomes a predetermined constant value.

In this case, it is preferable that the control unit may decide the predetermined constant value on the basis of the minimum resolution of the B mode acoustic image and a detection lower limit frequency in the acoustic wave detection unit.

In the photoacoustic image generation apparatus according to the invention, in a case where the detection frequency of the photoacoustic waves used in the case where the photoacoustic image is generated in the photoacoustic image generation unit exceeds a predetermined upper limit value, the control unit may perform a control of deciding the detection frequency of the photoacoustic waves used in the case where the photoacoustic image is generated in the photoacoustic image generation unit as the predetermined upper limit value and causing the image output unit to reduce the photoacoustic image generated by setting the detection frequency of the photoacoustic waves as the predetermined upper limit value and synthesize the reduced image with the B mode acoustic image.

In this case, it is preferable that the predetermined upper limit value is set to be equal to or less than a center frequency of the acoustic wave detection unit.

In the photoacoustic image generation apparatus according to the invention, a reference table holding unit that holds a reference table having recorded thereon a relationship between the resolution of the B mode acoustic image forming the display image and the detection frequency of the photoacoustic waves used in the case where the photoacoustic image is generated in the photoacoustic image generation unit may be further provided. The control unit may decide the detection frequency of the photoacoustic waves used in the case where the photoacoustic image is generated in the photoacoustic image generation unit on the basis of the reference table.

In the photoacoustic image generation apparatus according to the invention, it is preferable that the acoustic wave detection unit alternately detects the reflected acoustic waves for generating the B mode acoustic image and the photoacoustic waves for generating the photoacoustic image, and the image output unit outputs one display image on the basis of two images acquired in order of the B mode acoustic image and the photoacoustic image.

It is preferable that the insert is a needle that is inserted into the subject.

The photoacoustic image generation apparatus according to the invention can acquire the photoacoustic image with the appropriate resolution according to the resolution of the B mode ultrasound image since the detection frequency of the photoacoustic waves used in the case where the photoacoustic image is generated is controlled on the basis of the resolution of the B mode acoustic image forming the display image in the photoacoustic image generation apparatus that acquires both the B mode ultrasound image and the photoacoustic image, synthesizes both images, and outputs the synthesized image as the display image.

BRIEF DESCRIPTION OF THE DRAWINGS

FIG. 8 is a diagram illustrating an example of a reference table in the photoacoustic image generation apparatus according to the second embodiment.

DESCRIPTION OF THE PREFERRED EMBODIMENTS

Figure 1:
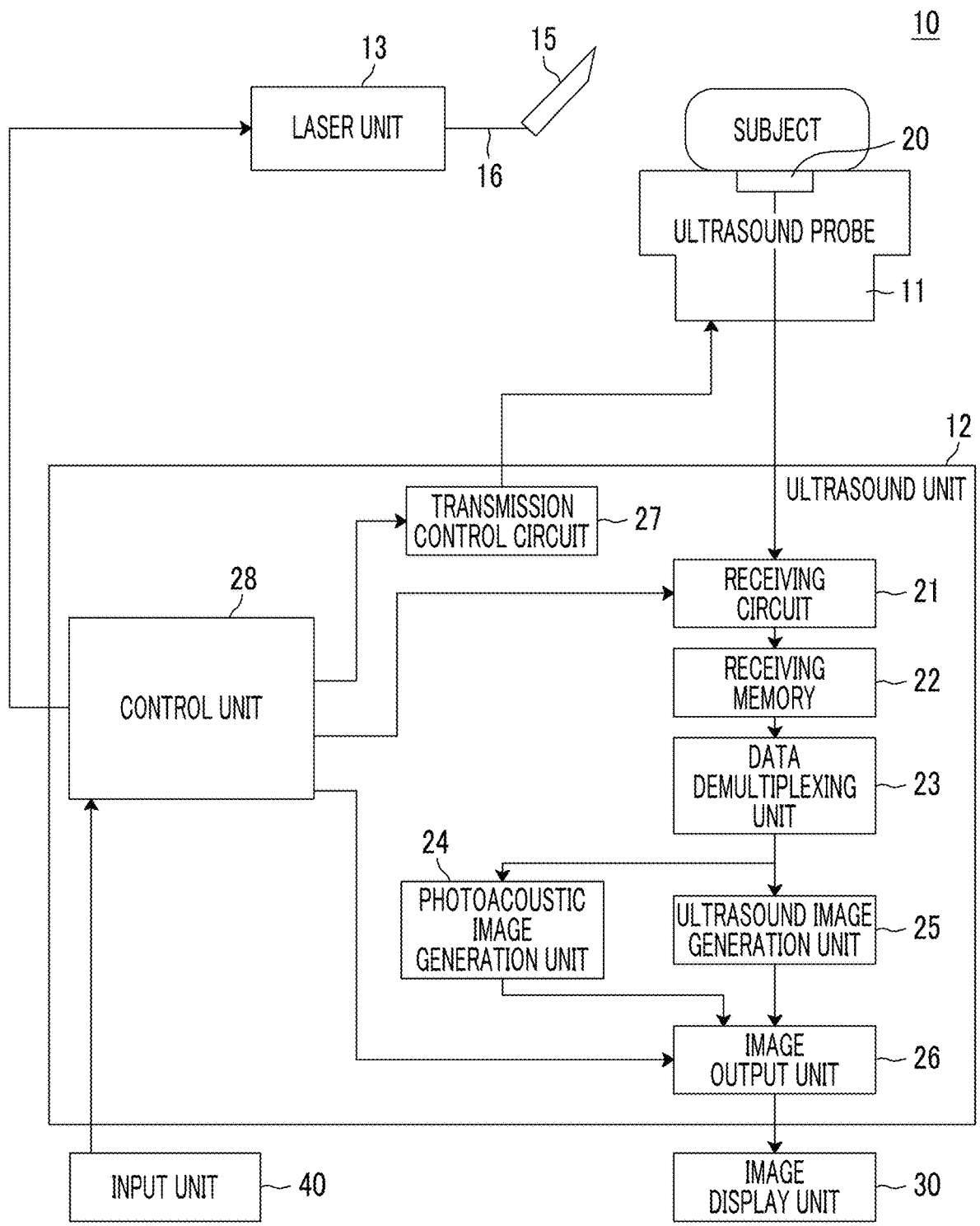
FIG. 1 is a block diagram schematically illustrating the configuration of a first embodiment of a photoacoustic image generation apparatus according to the invention.

Hereinafter, a first embodiment of a photoacoustic image generation apparatus according to the invention will be described in detail with reference to the drawings. FIG. 1 is a block diagram schematically illustrating the configuration of the first embodiment of the photoacoustic image generation apparatus according to the invention.

As illustrated in FIG. 1, a photoacoustic image generation apparatus 10 according to this embodiment comprises an ultrasound probe 11, an ultrasound unit 12, a laser unit 13, and a puncture needle 15. The puncture needle 15 and the laser unit 13 are connected by an optical cable 16 having an optical fiber. The puncture needle 15 can be attached to and detached from the optical cable 16 and is disposable. In addition, in this embodiment, ultrasonic waves are used as acoustic waves. However, the invention is not limited to the ultrasonic waves. Acoustic waves with an audible frequency may be used as long as an appropriate frequency can be selected according to, for example, an inspection target or measurement conditions.

The laser unit 13 comprises a solid-state laser light source using, for example, yttrium aluminum garnet (YAG) and alexandrite. Laser light emitted from the solid-state laser light source of the laser unit 13 is guided by the optical cable 16 and is incident on the puncture needle 15. The laser unit 13 according to this embodiment emits pulsed laser light in a near-infrared wavelength range. The near-infrared wavelength range means a wavelength range approximately from 700 nm to 850 nm. In this embodiment, the solid-state laser light source is used. However, other laser light sources, such as a gas laser light source, may be used or light sources other than the laser light source may be used.

Figure 2:
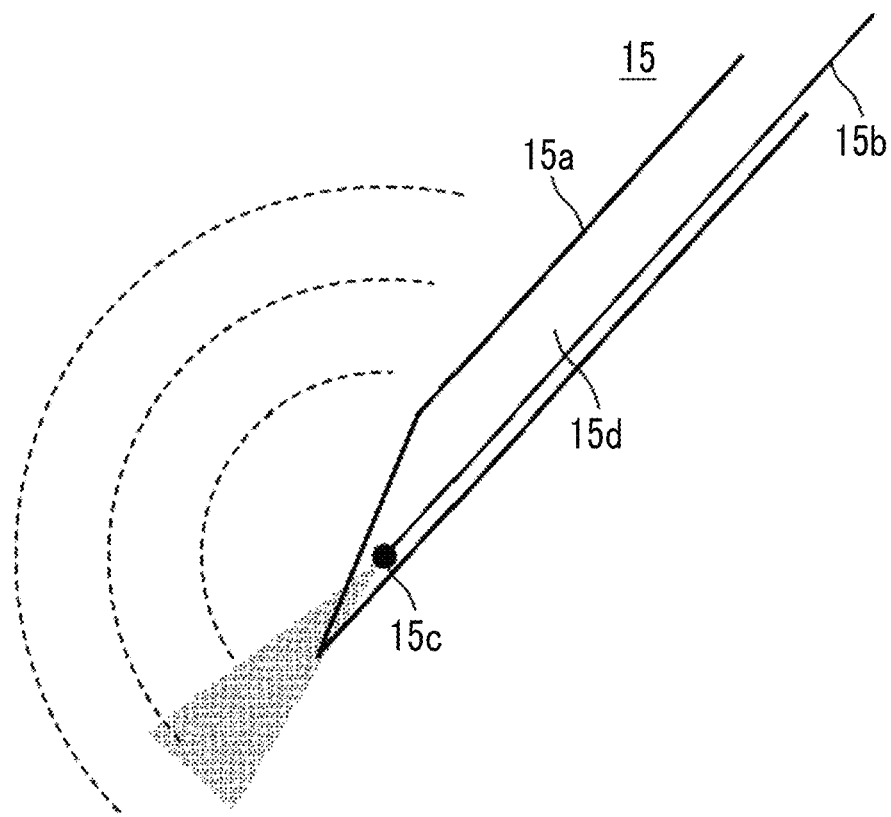
FIG. 2 is a cross-sectional view of the configuration of a tip portion of a puncture needle.

The puncture needle 15 is an embodiment of an insert according to the invention and is a needle that is inserted into a subject. FIG. 2 is a cross-sectional view including a center axis that extends in a length direction of the puncture needle 15. The puncture needle 15 includes a puncture needle main body 15a that has an opening at an acute tip and is formed in a hollow shape, an optical fiber 15b (corresponding to a light guide member according to the invention) that guides laser light emitted from the laser unit 13 to the vicinity of the opening of the puncture needle 15, and a photoacoustic wave generation portion 15c that absorbs laser light emitted from the optical fiber 15b and generates photoacoustic waves.

The optical fiber 15b and the photoacoustic wave generation portion 15c are disposed in a hollow portion 15d of the puncture needle main body 15a. For example, the optical fiber 15b is connected to the optical fiber in the optical cable 16 (see FIG. 1) through an optical connector that is provided at the base end of the puncture needle 15. For example, laser light of 0.2 mJ is emitted from a light emission end of the optical fiber 15b.

The photoacoustic wave generation portion 15c is provided at the light emission end of the optical fiber 15b and is provided in the vicinity of the tip of the puncture needle 15 and in the inner wall of the puncture needle main body 15a. The photoacoustic wave generation portion 15c absorbs the laser light emitted from the optical fiber 15b and generates photoacoustic waves. The photoacoustic wave generation portion 15c is made of, for example, an epoxy resin, a polyurethane resin, a fluorine resin, and silicone rubber with which a black pigment is mixed. In FIG. 2, the photoacoustic wave generation portion 15c is illustrated to be larger than the optical fiber 15b. However, the invention is not limited thereto. The photoacoustic wave generation portion 15c may have a size that is equal to the diameter of the optical fiber 15b.

The photoacoustic wave generation portion 15c is not limited to the above, and a metal film or an oxide film having light absorptivity with respect to the wavelength of laser light may be used as the photoacoustic wave generation portion. An oxide film made of, for example, iron oxide, chromium oxide, or manganese oxide having high light absorptivity with respect to the wavelength of laser light can be used as the photoacoustic wave generation portion 15c. Alternatively, a metal film made of, for example, titanium (Ti) or platinum (Pt) that has lower light absorptivity than an oxide and has higher biocompatibility than an oxide may be used as the photoacoustic wave generation portion 15c. In addition, the position where the photoacoustic wave generation portion 15c is provided is not limited to the inner wall of the puncture needle main body 15a. For example, a metal film or an oxide film which is the photoacoustic wave generation portion 15c may be formed on the light emission end of the optical fiber 15b with a thickness of about 100 nm by vapor deposition such that the oxide film covers the light emission end. In this case, at least a portion of the laser light emitted from the light emission end of the optical fiber 15b is absorbed by the metal film or the oxide film covering the light emission end and photoacoustic waves are generated from the metal film or the oxide film.

Returning to FIG. 1, the ultrasound probe 11 detects the photoacoustic waves emitted from the photoacoustic wave generation portion 15c after the puncture needle 15 is inserted into the subject. The ultrasound probe 11 comprises an acoustic wave detection unit 20 that detects the photoacoustic waves.

The acoustic wave detection unit 20 comprises a piezoelectric element array in which a plurality of piezoelectric elements that detect the photoacoustic waves are one-dimensionally arranged and a multiplexer. The piezoelectric element is an ultrasound transducer, and the ultrasound transducer is a piezoelectric element made of a polymer film such as piezoelectric ceramics or polyvinylidene fluoride (PVDF). The acoustic wave detection unit 20 comprises an acoustic lens, an acoustic matching layer, a backing member, a control circuit of the piezoelectric element array, and the like.

With the piezoelectric element array of the acoustic wave detection unit 20, the ultrasound probe 11 transmits the acoustic waves (ultrasonic waves) to the subject and receives the reflected acoustic waves (reflected ultrasonic waves) with respect to the transmitted ultrasonic waves, in addition to the detection of the photoacoustic waves. In addition, the transmission and reception of the ultrasonic waves may be performed at different positions. For example, ultrasonic waves may be transmitted from a position different from the ultrasound probe 11, and the piezoelectric element array of the ultrasound probe 11 may receive the reflected ultrasonic waves with respect to the transmitted ultrasonic waves. For example, a linear ultrasound probe, a convex ultrasound probe, or a sector ultrasound probe may be used as the ultrasound probe 11.

The ultrasound unit 12 includes the receiving circuit 21, a receiving memory 22, a data demultiplexing unit 23, a photoacoustic image generation unit 24, an ultrasound image generation unit 25, an image output unit 26, a transmission control circuit 27, and a control unit 28. The ultrasound unit 12 typically includes, for example, a processor, a memory, and a bus. In the ultrasound unit 12, a program related to, for example, a photoacoustic image generation process, an ultrasound image generation process, and a process of generating the display image obtained by synthesizing the ultrasound image and the photoacoustic image is incorporated into a memory. The program is operated by the control unit 28 which is formed by a processor to implement the functions of the data demultiplexing unit 23, the photoacoustic image generation unit 24, the ultrasound image generation unit 25, and the image output unit 26. That is, each of these units is formed by the memory into which the program has been incorporated and the processor.

The hardware configuration of the ultrasound unit 12 is not particularly limited and can be implemented by combining, for example, a plurality of integrated circuits (ICs), a processor, an application specific integrated circuit (ASIC), a field-programmable gate array (FPGA), and a memory as appropriate.

The receiving circuit 21 receives a detection signal output from the ultrasound probe 11 and stores the received detection signal in the receiving memory 22. The receiving circuit 21 typically includes a low-noise amplifier, a variable-gain amplifier, a low-pass filter, and an analog-to-digital convertor (AD convertor). The detection signal of the ultrasound probe 11 is amplified by the low-noise amplifier, is subjected to gain adjustment corresponding to a depth by the variable-gain amplifier, is converted into a digital signal by the AD convertor after a high-frequency component of the detection signal is cut by the low-pass filter, and then is stored in the receiving memory 22. The receiving circuit 21 is formed by, for example, one integrated circuit (IC).

The ultrasound probe 11 outputs a detection signal of the photoacoustic waves and a detection signal of the reflected ultrasonic waves. The receiving memory 22 stores the AD-converted detection signals (sampling data) of the photoacoustic waves and the reflected ultrasonic waves. The data demultiplexing unit 23 reads the detection signal of the photoacoustic waves from the receiving memory 22 and transmits the detection signal to the photoacoustic image generation unit 24. The data demultiplexing unit 23 reads the detection signal of the reflected ultrasonic waves from the receiving memory 22 and transmits the detection signal to the ultrasound image generation unit 25.

The photoacoustic image generation unit 24 generates a photoacoustic image on the basis of the detection signal of the photoacoustic waves detected by the ultrasound probe 11. The photoacoustic image generation process includes, for example, image reconfiguration such as phasing addition, detection, and logarithmic conversion. The ultrasound image generation unit 25 generates a B mode ultrasound image (corresponding to a B mode acoustic image according to the invention) that displays the internal state of the living body of the subject using a two-dimensional image on the basis of the detection signal of the reflected ultrasonic waves detected by the ultrasound probe 11. The B mode ultrasound image generation process also includes image reconfiguration such as phasing addition, detection, and logarithmic conversion. The image output unit 26 outputs the photoacoustic image and the B mode ultrasound image on an image display unit 30 such as a display apparatus.

The control unit 28 controls each component in the ultrasound unit 12. For example, in a case in which a photoacoustic image is acquired, the control unit 28 transmits a trigger signal to the laser unit 13 such that the laser unit 13 emits laser light. In addition, the control unit 28 transmits a sampling trigger signal to the receiving circuit 21 to control, for example, the sampling start time of the photoacoustic waves with the emission of the laser light. Sampling data received by the receiving circuit 21 is stored in the receiving memory 22.

The photoacoustic image generation unit 24 receives the sampling data of the detection signal of the photoacoustic waves through the data demultiplexing unit 23 and performs detection at a predetermined detection frequency to generate the photoacoustic image. The photoacoustic image generated by the photoacoustic image generation unit 24 is input to the image output unit 26.

In a case in which a B mode ultrasound image is acquired, the control unit 28 transmits an ultrasound transmission trigger signal for commanding the transmission control circuit 27 to transmit the ultrasonic waves. In a case in which the ultrasound transmission trigger signal is received, the transmission control circuit 27 causes the ultrasound probe 11 to transmit ultrasonic waves. In a case in which the ultrasound image is acquired, the ultrasound probe 11 performs a scanning while shifting a reception region of a group of piezoelectric elements line by line to detect the reflected ultrasonic waves by the control of the control unit 28. The control unit 28 transmits the sampling trigger signal to the receiving circuit 21 according to the transmission time of ultrasonic waves to start the sampling of the reflected ultrasonic waves. The sampling data received by the receiving circuit 21 is stored in the receiving memory 22.

The ultrasound image generation unit 25 receives the sampling data of the detection signal of the photoacoustic waves through the data demultiplexing unit 23 and performs the detection at a predetermined detection frequency to generate the B mode ultrasound image. The B mode ultrasound image generated by the ultrasound image generation unit 25 is input to the image output unit 26.

The image output unit 26 synthesizes the photoacoustic image generated by the photoacoustic image generation unit 24 and the B mode ultrasound image generated by the ultrasound image generation unit 25 to generate the display image and outputs the generated display image on the image display unit 30 such as a display apparatus. The image output unit 26 can individually output and display the photoacoustic image and the B mode ultrasound image on the image display unit 30 without synthesizing both images.

Figure 3:
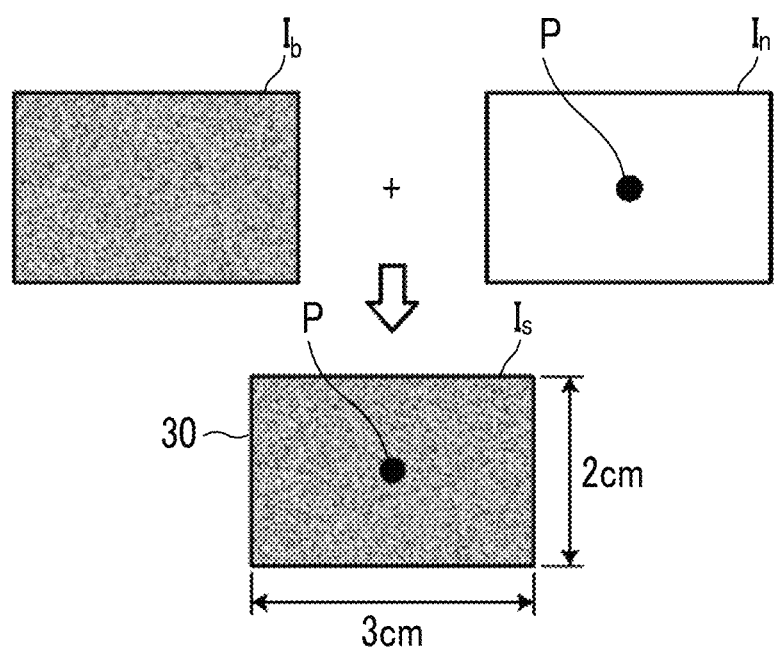
FIG. 3 is a diagram illustrating an example of a display image.
Figure 4:
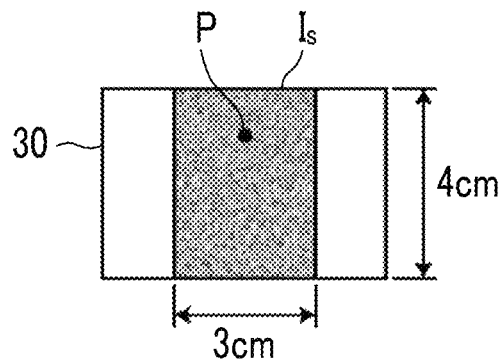
FIG. 4 is a diagram illustrating another example of the display image.

Here, a generation method of the display image by the control unit 28 will be described in detail. FIG. 3 is a diagram illustrating an example of the display image, and FIG. 4 is a diagram illustrating another example of the display image.

As illustrated in FIG. 3, a display image $I_s$ is generated by superimposing a photoacoustic image $I_n$ on a B mode ultrasound image $I_b$. In this embodiment, it is assumed that one display image $I_s$ is generated on the basis of two images acquired in order of the B mode ultrasound image $I_b$ and the photoacoustic image $I_n$.

It is assumed that the detection frequency at the time of the generation of the B mode ultrasound image $I_b$ is controlled according to the depth of the living body tissue of the subject. The detection frequency at the time of the generation of the photoacoustic image $I_n$ has a fixed initial value according to the depth, but the value is changed by the control at the time of the generation of the display image $I_s$ described below. In this description, it is assumed that $f_b$ is the detection frequency (MHz) at the time of the generation of the B mode ultrasound image $I_b$, $R_b$ is the resolution (pixel/mm) of the B mode ultrasound image $I_b$, and $f_n$ is the detection frequency (MHz) at the time of the generation of the photoacoustic image $I_n$.

For example, in a case where the sound speed c in the living body is 1500 m/s (normally, the sound speed in the living body is about 1540 m/s, but it is simplified herein), the initial value $f_n$ of the detection frequency at the time of the generation of the photoacoustic image $I_n$ is 5 MHz (wavelength $\lambda_n$=300 µm), and the number of pixels in the longitudinal direction of an image display region of the image display unit 30 is 400 pixels, and as illustrated in FIG. 3, a display image $I_s$ of a living body tissue having 3 cm (30 mm) in the lateral direction×2 cm (20 mm) in the depth direction is displayed such that a depth display direction of the display image $I_s$ is the entire longitudinal direction of the image display region of the image display unit 30, the resolution $R_b$ of the B mode ultrasound image $I_b$ is 20 pixels/mm as follows.

$R_b$=400(pixels)/20(mm)=20(pixels/mm)

The number of pixels on which one wavelength of the detection frequency at the time of the generation of the photoacoustic image $I_n$ is displayed is six pixels as follows.

20(pixels/mm)×0.3(mm)=6(pixels)

As illustrated in FIG. 4, in a case where a display image $I_s$ of a living body tissue having 3 cm (30 mm) in the lateral direction×4 cm (40 mm) in the depth direction is displayed such that the depth display direction of the display image $I_s$ is the entire longitudinal direction of the image display region of the image display unit 30, the resolution $R_b$ of the B mode ultrasound image $I_b$ is 10 pixels/mm as follows.

$R_b$=400(pixels)/40(mm)=10(pixels/mm)

The number of pixels on which one wavelength of the detection frequency at the time of the generation of the photoacoustic image $I_n$ is displayed is three pixels as follows.

10(pixels/mm)×0.3(mm)=3(pixels)

A setting of a display range of the display image $I_s$ as described above is input to the control unit 28 through an input unit 40 by a user.

In this way, in a case where there is a difference in the resolution of the display image $I_s$, a tradeoff occurs between $f_n$ and $R_b$ in a case where the detection frequency $f_n$ at the time of the generation of the photoacoustic image $I_n$ is a fixed value. As illustrated in FIGS. 3 and 4, the tip position of the puncture needle 15 is commonly displayed by a bright point P in the photoacoustic image $I_n$ indicating the tip position of the puncture needle 15. However, since the display size of the bright point P depends on the detection frequency (wavelength) of the photoacoustic wave signal at the time of the generation of the photoacoustic image $I_n$ and thus the image size for one wavelength, which is the minimum resolution, becomes larger as the detection frequency is lower (wavelength is longer), the tip position thereof is displayed by a large bright point P.

In a case where the diameter of about three pixels illustrated in FIG. 4 is considered to be optimum as the display size of the bright point P, the detection frequency $f_n$ at the time of the generation of the photoacoustic image $I_n$ becomes too small with respect to the resolution $R_b$ of the B mode ultrasound image $I_b$ in the example illustrated in FIG. 3 and thus the display size of the bright point P becomes too large at the diameter of about six pixels. Therefore, there may be a problem that a region of the B mode ultrasound image $I_b$ hidden by the bright point P becomes wide and thus it is difficult to view the living body tissue around the tip of the puncture needle 15.

Conversely, in a case where the detection frequency $f_n$ at the time of the generation of the photoacoustic image $I_n$ becomes too large with respect to the resolution $R_b$ of the B mode ultrasound image $I_b$, there may be a problem that the display size of the bright point P becomes too small and thus it is difficult to check the tip position of the puncture needle 15. For example, in a case where the resolution $R_b$ of the B mode ultrasound image $I_b$ is 10 pixels/mm similar to the example of FIG. 4 and the detection frequency $f_n$ at the time of the generation of the photoacoustic image $I_n$ is changed to 10 MHz (wavelength $\lambda_n$=150 µm), the number of pixels on which one wavelength of the detection frequency at the time of the generation of the photoacoustic image $I_n$ is displayed is 1.5 pixels.

That is, there is an optimum detection frequency $f_n$ at the time of the generation of the photoacoustic image $I_n$ for image display with respect to the resolution $R_b$ of the B mode ultrasound image $I_b$.

In the photoacoustic image generation apparatus 10 according to this embodiment, the detection frequency $f_n$ at the time of the generation of the photoacoustic image $I_n$ is decided such that the product of the resolution $R_b$ of the B mode ultrasound image $I_b$ and the wavelength $\lambda_n$ at the detection frequency $f_n$ at the time of the generation of the photoacoustic image $I_n$ is a predetermined constant value (const) as described below. That is, the detection frequency $f_n$ at the time of the generation of the photoacoustic image $I_n$ is controlled to be higher as the resolution $R_b$ of the B mode ultrasound image $I_b$ becomes higher. Here, $\alpha$ is a bright point display size adjustment parameter.

$R_b \times \lambda_n \times \alpha$=(const)

In a case where the above equation is rewritten as an equation of the detection frequency $f_n$ at the time of the generation of the photoacoustic image $I_n$, the following equation (1) is obtained.

$R_b \times c/f_n$=(const)/$\alpha$ $f_n = R_b \times c \times \alpha/$(const)+$\delta$     (1)

Since the detection frequency $f_n$ that can be handled by the apparatus has a discrete value due to the limitation of the number of clocks, there may be a case where $f_n$ cannot be a value (here, f) obtained from equation (1) excluding $\delta$. The $\delta$ in equation (1) is an adjustment parameter for adjusting such an error and is obtained as follows. Here, Mod[frx_clock,f] is the remainder at the time of dividing a reception clock frequency frx_clock by f.

$\delta = f_n \times f \times$Mod[$frx\_clock, f$]

In this way, the detection frequency $f_n$ at the time of the generation of the photoacoustic image $I_n$ is decided according to the resolution $R_b$ of the B mode ultrasound image $I_b$ by equation (1). Thus, it is possible to make the display size of the bright point P constant without depending on the change in the resolution $R_b$.

As described above, in the case where the detection frequency $f_b$ at the time of the generation of the B mode ultrasound image $I_b$ is controlled according to the depth of the living body tissue of the subject, the detection frequency $f_b$ is decided by a transmission frequency in the ultrasound probe 11 and a depth position of the living body tissue. Basically, for the detection frequency $f_b$, the transmission frequency is used in the shallowest region in a detection range and a lower limit frequency of the ultrasound probe 11 is used in the deepest region in the detection range. Therefore, an upper limit value of the detection frequency $f_b$ is decided by a transmission condition, and a lower limit value thereof is decided by the performance of the ultrasound probe 11.

Since there is no transmission from the ultrasound probe 11 and there is only reception in the ultrasound probe 11 at the time of the generation of the photoacoustic image $I_n$, it is desirable that the lower limit value of the detection frequency $f_b$ is uniquely decided by the performance of the ultrasound probe 11.

Therefore, it is preferable that the predetermined constant value (const) is decided on the basis of the minimum resolution $R_{b\_MIN}$ of the B mode ultrasound image $I_b$ and a detection lower limit frequency $f_{MIN}$ in the ultrasound probe 11.

$$(\text{const}) = R_{b\_MIN} \times c / f_{MIN} \times \alpha$$

Here, the detection lower limit frequency $f_{MIN}$ indicates the minimum value of the detection frequency $f_b$ at the time of the generation of the B mode ultrasound image $I_b$. Since the same reception signal from the ultrasound probe 11 is used also for the photoacoustic image $I_n$, the minimum value of the detection frequency is the lowest frequency part of a frequency band (for example, −20 dB band) usable by the ultrasound probe 11 and the value is the same value as the B mode ultrasound image $I_b$.

Figure 5:
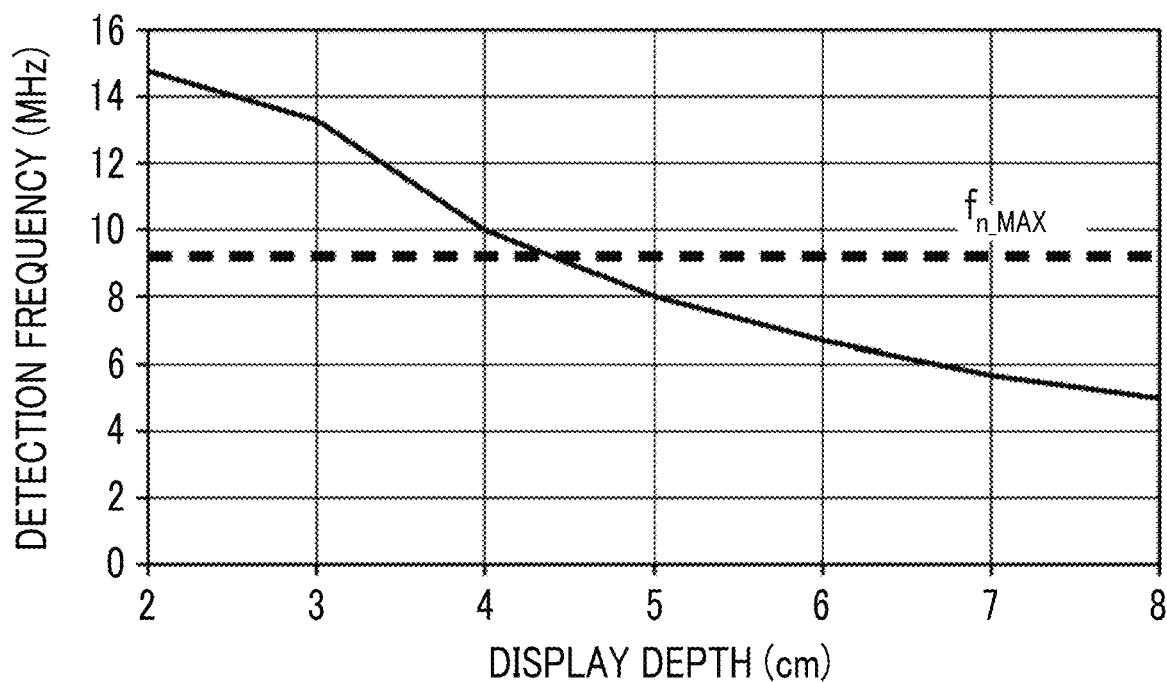
FIG. 5 is a graph illustrating a relationship between a detection frequency of photoacoustic waves and display depth.

This point will be described with a specific example. FIG. 5 is a graph illustrating a relationship between the detection frequency of the photoacoustic waves and the display depth. In a case where the maximum detection depth of the living body tissue of the subject is 8 cm and a display image $I_s$ of a living body tissue having 8 cm (80 mm) in the depth direction is displayed such that the depth display direction of the display image $I_s$ is the entire longitudinal direction (400 pixels) of the image display region of the image display unit 30 similar to the above, the minimum resolution $R_{b\_MIN}$ of the B mode ultrasound image $I_b$ is 5 pixels/mm as follows. In a case where the detection lower limit frequency $f_{MIN}$ is 5 MHz (wavelength $\lambda_n = 300$ μm) and the bright point display size adjustment parameter $\alpha$ is one, the display size (const) of the bright point P is 1.5 pixels.

$$(\text{const}) = 5(\text{pixels}/mm) \times 0.3(mm) \times 1 = 1.5(\text{pixels})$$

There may also be a case where the display depth exceeds 16 cm or 20 cm depending on a type of the ultrasound probe 11 and an observation target (such as abdomen). In a case where the number of pixels (400 pixels) in the entire longitudinal direction of the image display region of the image display unit 30 and the detection lower limit frequency $f_{MIN}$ of 5 MHz (wavelength $\lambda_n = 300$ μm) are the same, the display size (const) of the bright point P is 0.75 pixel in the case of the maximum display depth of 16 cm and the display size (const) of the bright point P is 0.6 pixel in the case of the maximum display depth of 20 cm. In the case where the display size of the bright point P becomes too small as described above, it is possible to adjust the display size of the bright point P by adjusting the bright point display size adjustment parameter $\alpha$.

Since the bright point P indicating the tip position of the puncture needle 15 in the photoacoustic image $I_n$ is displayed as a point, it is important to grasp the position surely rather than acquiring detailed image information. Since a signal with high depth reachability can be received at a lower frequency as the detection frequency at the time of the generation of the photoacoustic image $I_n$, a stable image display is possible.

Therefore, in a case where the detection frequency $f_n$ at the time of the generation of the photoacoustic image $I_n$ obtained by equation (1) exceeds a predetermined upper limit value $f_{n\_MAX}$ as illustrated in the graph of FIG. 5, it is preferable that the detection frequency of the photoacoustic waves used in the case where the photoacoustic image $I_n$ is generated is decided as $f_{n\_MAX}$ and the photoacoustic image $I_n$ generated by setting the detection frequency of the photoacoustic waves as $f_{n\_MAX}$ is reduced and synthesized with the B mode ultrasound image.

In this case, it is preferable that the predetermined upper limit value $f_{n\_MAX}$ is set to be equal to or less than a center frequency of the ultrasound probe 11. Accordingly, a stable image display is possible.

A reduction ratio (image size after reduction/image size before reduction) $R_R$ in the case where the photoacoustic image $I_n$ generated by setting the detection frequency of the photoacoustic waves as $f_{n\_MAX}$ is reduced is obtained by the following equation (2).

$$R_R = f_{n\_MAX} / f_n \quad (2)$$

In the case of reducing the photoacoustic image $I_n$, the reduction is performed by setting the center position of the bright point P in the photoacoustic image $I_n$ as the center. Since the B mode ultrasound image $I_b$ becomes different from the photoacoustic image $I_n$ in the image size in the case where the photoacoustic image $I_n$ is reduced, it is impossible to simply synthesize the B mode ultrasound image $I_b$ and the photoacoustic image $I_n$.

In a case where the reduced photoacoustic image $I_n$ is synthesized with the B mode ultrasound image $I_b$, a center position coordinate of the bright point P in the case of superimposing the photoacoustic image $I_n$ on the B mode ultrasound image $I_b$ and an image around the bright point P may be needed. Therefore, only these pieces of information may be acquired.

For the image around the bright point P, for example, in a case where the display size (const) of the bright point P is three pixels and the detection frequency $f_n$ of the photoacoustic waves used in the case where the photoacoustic image $I_n$ is generated is suppressed to $f_{n\_MAX}$ which is the frequency lower than the detection frequency $f_n$ obtained by equation (1), the display size of the bright point P in the photoacoustic image $I_n$ acquired at the detection frequency $f_{n\_MAX}$ becomes larger than three pixels. Therefore, an image range around the bright point may be set slightly wider in consideration of the reduction ratio $R_R$. For example, in a case where the reduction ratio $R_R$ is 0.5 with respect to the final display size (const) of the bright point P of three pixels, only an image having a region of six pixels×six pixels may be acquired.

Figure 6:
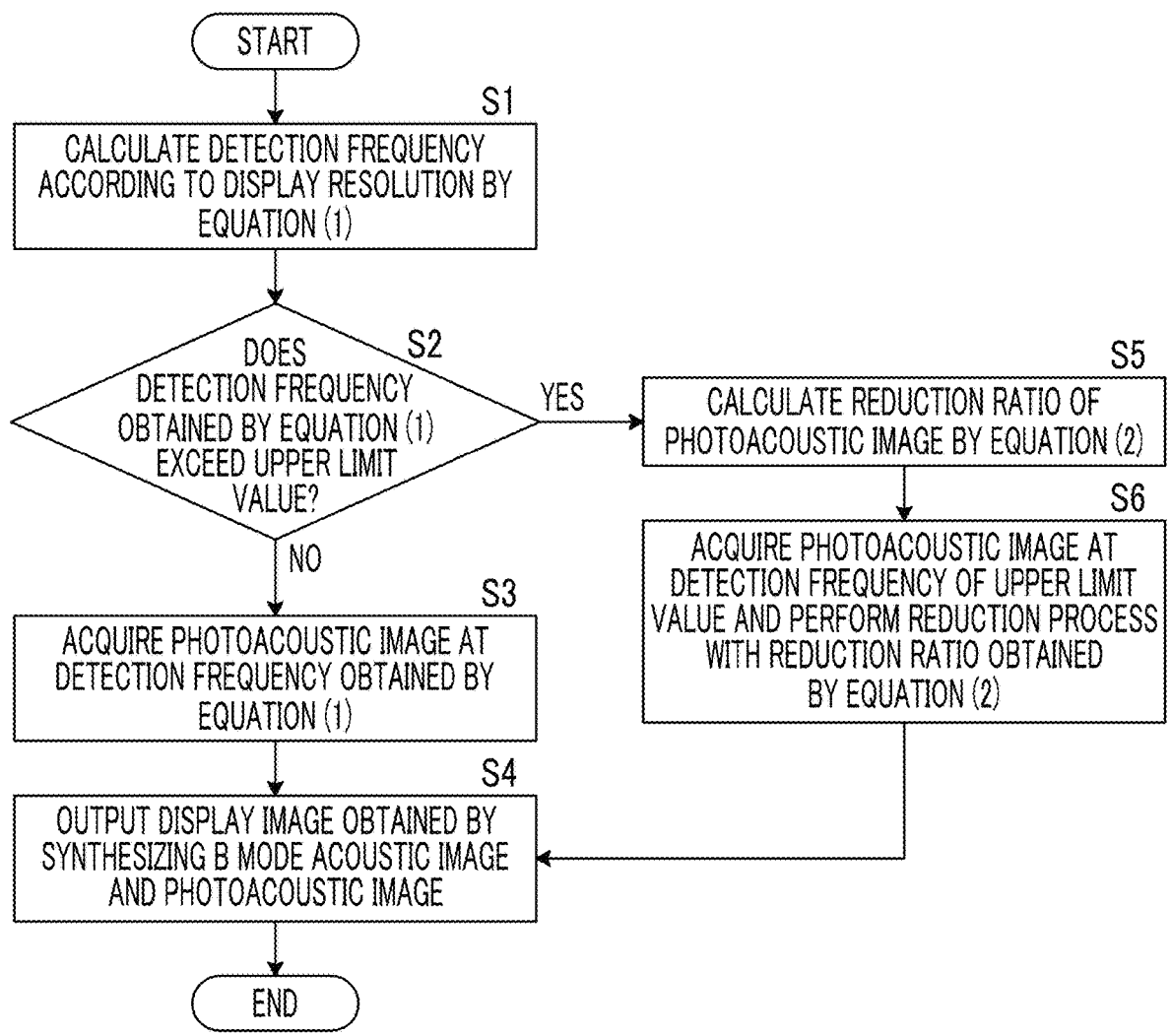
FIG. 6 is a flowchart for describing a generation method of the display image in the photoacoustic image generation apparatus according to the first embodiment.

On the basis of the above, in this embodiment, the generation of the display image $I_s$ by the control unit 28 is performed according to a procedure of a flowchart illustrated in FIG. 6.

First, the control unit 28 calculates the detection frequency $f_n$ at the time of the generation of the photoacoustic image $I_n$ according to the resolution $R_b$ of the B mode ultrasound image $I_b$ by equation (1) described above (S1) and determines whether the detection frequency $f_n$ obtained by equation (1) exceeds the upper limit value (S2).

In a case where the calculated detection frequency $f_n$ does not exceed the predetermined upper limit value, the control unit 28 causes the photoacoustic image generation unit 24 to generate the photoacoustic image $I_n$ at the calculated detection frequency $f_n$ (S3) and causes the image output unit 26 to output the display image $I_s$ obtained by synthesizing the B mode ultrasound image $I_b$ and the photoacoustic image $I_n$ (S4).

In a case where the calculated detection frequency $f_n$ exceeds the predetermined upper limit value, the control unit 28 calculates the reduction ratio of the photoacoustic image $I_n$ by equation (2) described above (S5), causes the photoacoustic image generation unit 24 to generate the photoacoustic image $I_n$ at the detection frequency $f_{n\_MAX}$ of the predetermined upper limit value, causes the image output unit 26 to perform a reduction process on the photoacoustic image $I_n$ with the reduction ratio obtained by equation (2) (S6), and causes the image output unit 26 to output the display image $I_s$ obtained by synthesizing the B mode ultrasound image $I_b$ and the reduced photoacoustic image $I_n$ (S4).

With such a configuration, an appropriate detection frequency $f_n$ at the time of the generation of the photoacoustic image $I_n$ can be set according to the resolution $R_b$ of the B mode ultrasound image $I_b$ and the photoacoustic image $I_n$ with an appropriate resolution can be acquired. Therefore, it is possible to set the size of the bright point P in the photoacoustic image $I_n$ superimposed on the B mode ultrasound image $I_b$ to an appropriate size.

Figure 7:
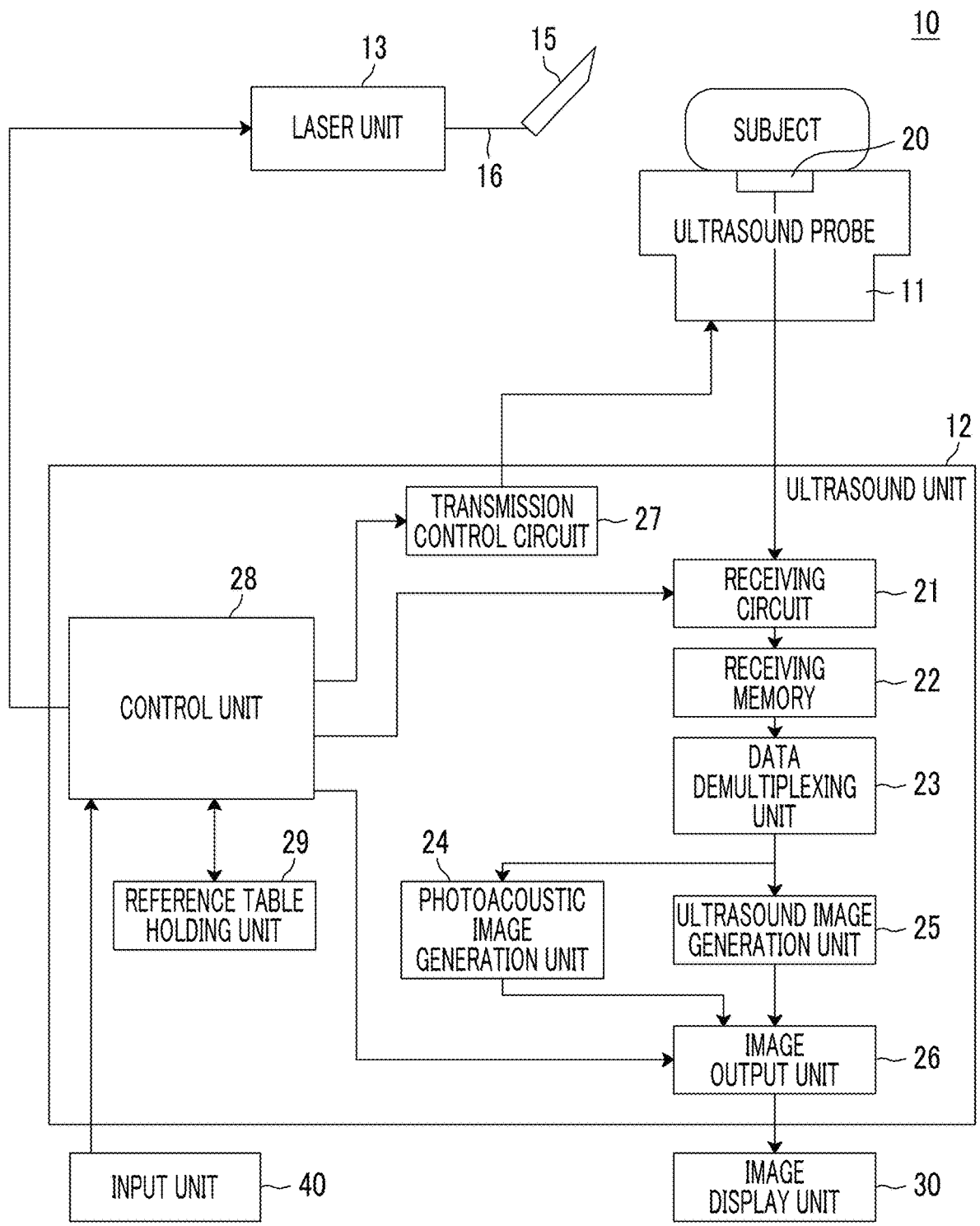
FIG. 7 is a block diagram schematically illustrating the configuration of a second embodiment of the photoacoustic image generation apparatus according to the invention.
Figure 8:
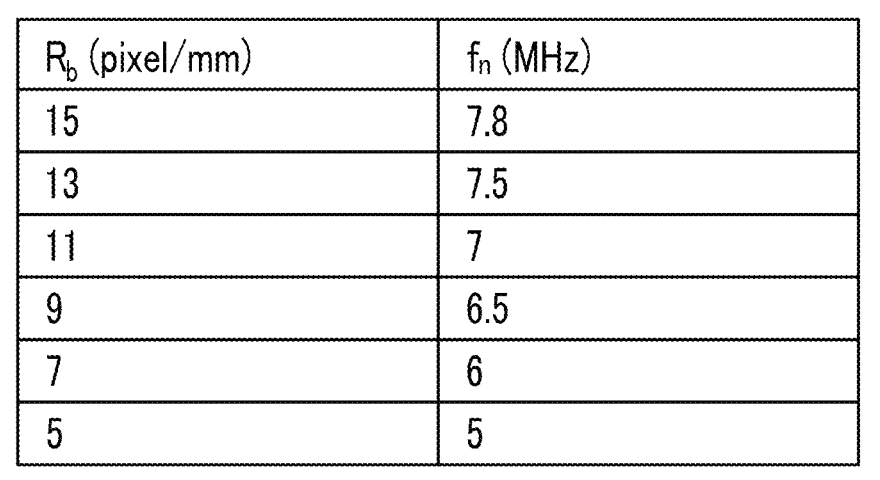

Next, a second embodiment of the photoacoustic image generation apparatus according to the invention will be described. In the photoacoustic image generation apparatus 10 according to the first embodiment, the detection frequency $f_n$ at the time of the generation of the photoacoustic image $I_n$ according to the resolution $R_b$ of the B mode ultrasound image $I_b$ is decided by the predetermined calculation equation. However, in the photoacoustic image generation apparatus 10 according to the second embodiment, the detection frequency $f_n$ at the time of the generation of the photoacoustic image $I_n$ according to the resolution $R_b$ of the B mode ultrasound image $I_b$ is decided on the basis of a reference table prepared in advance. Other configurations and actions are the same as those in the photoacoustic image generation apparatus 10 according to the first embodiment. FIG. 7 is a block diagram schematically illustrating the configuration of the second embodiment of the photoacoustic image generation apparatus according to the invention. FIG. 8 is a diagram illustrating an example of the reference table in the photoacoustic image generation apparatus according to the second embodiment.

The photoacoustic image generation apparatus 10 according to the second embodiment comprises a reference table holding unit 29 that holds a reference table, such as the reference table illustrated in FIG. 8 as an example, recording a relationship between the resolution $R_b$ of the B mode ultrasound image $I_b$ and the detection frequency $f_n$ at the time of the generation of the photoacoustic image $I_n$. The reference table holding unit 29 can be implemented by, for example, a memory or the like. In the case of generating the display image $I_s$, the control unit 28 decides the detection frequency $f_n$ at the time of the generation of the photoacoustic image $I_n$ on the basis of the reference table held in the reference table holding unit 29. With such a configuration, it is also possible to obtain the same effect as the photoacoustic image generation apparatus 10 according to the first embodiment.

In the above-described first and second embodiments, the puncture needle 15 is used as an embodiment of the insert. However, the invention is not limited thereto as the insert. The insert may be a radio-frequency ablation needle including an electrode that is used for radio-frequency ablation therein, a catheter that is inserted into a blood vessel, or a guide wire for a catheter that is inserted into a blood vessel. Alternatively, the insert may be an optical fiber for laser treatment.

The insert is not limited to a needle, such as an injection needle, and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen.

The invention has been described above on the basis of the preferred embodiments. However, the photoacoustic image generation apparatuses according to the invention are not limited only to the above-described embodiments. Various modifications and changes of the configurations according to the above-described embodiments are also included in the scope of the invention.

EXPLANATION OF REFERENCES

10: photoacoustic image generation apparatus
11: ultrasound probe
12: ultrasound unit
13: laser unit
15: puncture needle
15a: puncture needle main body
15b: optical fiber
15c: photoacoustic wave generation portion
15d: hollow portion
16: optical cable
20: acoustic wave detection unit
21: receiving circuit
22: receiving memory
23: data demultiplexing unit
24: photoacoustic image generation unit
25: ultrasound image generation unit
26: image output unit
27: transmission control circuit
28: control unit
29: reference table holding unit
30: image display unit
40: input unit
$I_b$: B mode ultrasound image
$I_n$: photoacoustic image
$I_s$: display image
P: bright point

What is claimed is:

1. A photoacoustic image generation apparatus comprising:
an insert of which at least a tip portion is adapted to be inserted into a subject and which includes a light guide that guides light to the tip portion and a photoacoustic wave generation portion that absorbs the light guided by the light guide and generates photoacoustic waves;
an ultrasound probe that detects the photoacoustic waves emitted from the photoacoustic wave generation portion and detects reflected acoustic waves reflected by transmission of acoustic waves to the subject; and
a processor,
wherein the processor configured to:

generate a B mode acoustic image on the basis of the reflected acoustic waves detected by the ultrasound probe, generate a photoacoustic image on the basis of the photoacoustic waves detected by the ultrasound probe, output a display image obtained by synthesizing the B mode acoustic image and the photoacoustic image, determine a resolution of the B mode acoustic image, and control a detection frequency of the photoacoustic waves used in a case where the photoacoustic image is generated based on the resolution of the B mode acoustic image forming the display image in order to change a size of bright point indicating the tip of the insert in the photoacoustic image forming the display image.

2. The photoacoustic image generation apparatus according to claim 1, wherein the processor further configured to control the detection frequency of the photoacoustic waves used in the case where the photoacoustic image is generated to be higher as the resolution of the B mode acoustic image forming the display image becomes higher.

3. The photoacoustic image generation apparatus according to claim 2, wherein the processor further configured to decide the detection frequency of the photoacoustic waves used in the case where the photoacoustic image is generated such that a product of the resolution ($R_b$) of the B mode acoustic image forming the display image, a bright point display size adjustment parameter ($\alpha$), and a wavelength ($\lambda_n$) at the detection frequency of the photoacoustic waves used in the case where the photoacoustic image is generated becomes a predetermined constant value, where $$R_b \times \lambda_n \times \alpha = (\text{const}).$$

4. The photoacoustic image generation apparatus according to claim 3, wherein the processor further configured to decide the predetermined constant value on the basis of the minimum resolution of the B mode acoustic image and a detection lower limit frequency in the ultrasound probe.

5. The photoacoustic image generation apparatus according to claim 4, wherein in a case where the detection frequency of the photoacoustic waves used in the case where the photoacoustic image is generated exceeds a predetermined upper limit value, the processor further configured to decide the detection frequency of the photoacoustic waves used in the case where the photoacoustic image is generated as the predetermined upper limit value, reduce the photoacoustic image generated by setting the detection frequency of the photoacoustic waves as the predetermined upper limit value, and synthesize the reduced image with the B mode acoustic image.

6. The photoacoustic image generation apparatus according to claim 5, wherein the predetermined upper limit value is set to be equal to or less than a center frequency of the ultrasound probe.

7. The photoacoustic image generation apparatus according to claim 3, wherein in a case where the detection frequency of the photoacoustic waves used in the case where the photoacoustic image is generated exceeds a predetermined upper limit value, the processor further configured to decide the detection frequency of the photoacoustic waves used in the case where the photoacoustic image is generated as the predetermined upper limit value, reduce the photoacoustic image generated by setting the detection frequency of the photoacoustic waves as the predetermined upper limit value, and synthesize the reduced image with the B mode acoustic image.

8. The photoacoustic image generation apparatus according to claim 7, wherein the predetermined upper limit value is set to be equal to or less than a center frequency of the ultrasound probe.

9. The photoacoustic image generation apparatus according to claim 2, further comprising:

a reference table memory that holds a reference table having recorded thereon a relationship between the resolution of the B mode acoustic image forming the display image and the detection frequency of the photoacoustic waves used in the case where the photoacoustic image is generated, wherein the processor further configured to decide the detection frequency of the photoacoustic waves used in the case where the photoacoustic image is generated on the basis of the reference table.

10. The photoacoustic image generation apparatus according to claim 2, wherein the ultrasound probe alternately detects the reflected acoustic waves for generating the B mode acoustic image and the photoacoustic waves for generating the photoacoustic image, and wherein the processor further configured to output one display image on the basis of two images acquired in order of the B mode acoustic image and the photoacoustic image.

11. The photoacoustic image generation apparatus according to claim 1, wherein the processor further configured to decide the detection frequency of the photoacoustic waves used in the case where the photoacoustic image is generated such that a product of the resolution ($R_b$) of the B mode acoustic image forming the display image, a bright point display size adjustment parameter ($\alpha$), and a wavelength ($\lambda_n$) at the detection frequency of the photoacoustic waves used in the case where the photoacoustic image is generated becomes a predetermined constant value, where $$R_b \times \lambda \times \alpha = (\text{const}).$$

12. The photoacoustic image generation apparatus according to claim 11, wherein the processor further configured to decide the predetermined constant value on the basis of the minimum resolution of the B mode acoustic image and a detection lower limit frequency in the ultrasound probe.

13. The photoacoustic image generation apparatus according to claim 12, wherein in a case where the detection frequency of the photoacoustic waves used in the case where the photoacoustic image is generated exceeds a predetermined upper limit value, the processor further configured to decide the detection frequency of the photoacoustic waves used in the case where the photoacoustic image is generated as the predetermined upper limit value, reduce the photoacoustic image generated by setting the detection frequency of the photoacoustic waves as the predetermined upper limit value, and synthesize the reduced image with the B mode acoustic image.

14. The photoacoustic image generation apparatus according to claim 13, wherein the predetermined upper limit value is set to be equal to or less than a center frequency of the ultrasound probe.

15. The photoacoustic image generation apparatus according to claim 11,
wherein in a case where the detection frequency of the photoacoustic waves used in the case where the photoacoustic image is generated exceeds a predetermined upper limit value, the processor further configured to decide the detection frequency of the photoacoustic waves used in the case where the photoacoustic image is generated as the predetermined upper limit value, reduce the photoacoustic image generated by setting the detection frequency of the photoacoustic waves as the predetermined upper limit value, and synthesize the reduced image with the B mode acoustic image.

16. The photoacoustic image generation apparatus according to claim 15,
wherein the predetermined upper limit value is set to be equal to or less than a center frequency of the ultrasound probe.

17. The photoacoustic image generation apparatus according to claim 11,
wherein the ultrasound probe alternately detects the reflected acoustic waves for generating the B mode acoustic image and the photoacoustic waves for generating the photoacoustic image, and
wherein the processor further configured to output one display image on the basis of two images acquired in order of the B mode acoustic image and the photoacoustic image.

18. The photoacoustic image generation apparatus according to claim 1, further comprising:
a reference table memory that holds a reference table having recorded thereon a relationship between the resolution of the B mode acoustic image forming the display image and the detection frequency of the photoacoustic waves used in the case where the photoacoustic image is generated,
wherein the processor further configured to decide the detection frequency of the photoacoustic waves used in the case where the photoacoustic image is generated on the basis of the reference table.

19. The photoacoustic image generation apparatus according to claim 1,
wherein the ultrasound probe alternately detects the reflected acoustic waves for generating the B mode acoustic image and the photoacoustic waves for generating the photoacoustic image, and
wherein the processor further configured to output one display image on the basis of two images acquired in order of the B mode acoustic image and the photoacoustic image.

20. The photoacoustic image generation apparatus according to claim 1,
wherein the insert is a needle that is adapted to be inserted into the subject.

* * * * *